US008958864B2

(12) United States Patent
Amies et al.

(10) Patent No.: US 8,958,864 B2
(45) Date of Patent: Feb. 17, 2015

(54) COMBINED RADIATION THERAPY AND MAGNETIC RESONANCE UNIT (75) Inventors: Christopher Jude Amies, Walnut Creek, CA (US); Paul Beasley, Abingdon (GB); Juan Carlos Celi, Bensheim (DE); Oliver Heid, Gunzenhausen (DE); Francisco Miguel Hernandez-Guerra, Danville, CA (US); Marcel Jan Marie Kruip, Oxford (GB); Markus Vester, Nürnberg (DE)

(73) Assignees: Siemens Aktiengesellschaft, München (DE); Siemens Medical Solutions USA, Inc, Malvern, PA (US)

( * ) Notice: Subject to any disclaimer, the term of this patent is extended or adjusted under 35 U.S.C. 154(b) by 1600 days.

(21) Appl. No.: 12/072,851

(22) Filed: Feb. 28, 2008

(65) Prior Publication Data
US 2008/0208036 A1 Aug. 28, 2008

(30) Foreign Application Priority Data

Feb. 28, 2007 (DE) .......................... 10 2007 010 132
Feb. 1, 2008 (DE) .......................... 10 2008 007 245

(51) Int. Cl.
*A61B 6/00* (2006.01)
*A61B 5/055* (2006.01)
(52) U.S. Cl.
USPC .......................................................... 600/411
(58) Field of Classification Search
None
See application file for complete search history.

(56) References Cited

U.S. PATENT DOCUMENTS

| 3,969,629 | A  | * | 7/1976  | McIntyre ........................ 378/65 |
| 5,153,546 | A  | * | 10/1992 | Laskaris ....................... 335/216 |
| 5,757,885 | A  |   | 5/1998  | Harroun |
| 6,366,798 | B2 | * | 4/2002  | Green ........................... 600/411 |
| 6,385,481 | B2 | * | 5/2002  | Nose et al. .................... 600/415 |
| 6,487,274 | B2 |   | 11/2002 | Bertsche |
| 6,812,700 | B2 | * | 11/2004 | Fahrig et al. .................. 324/318 |
| 6,925,319 | B2 |   | 8/2005  | McKinnon |
| 6,977,987 | B2 | * | 12/2005 | Yamashita et al. .............. 378/64 |
| 7,394,254 | B2 | * | 7/2008  | Rieke et al. ................... 324/318 |
| 8,055,325 | B1 | * | 11/2011 | Damadian et al. ............ 600/421 |
| 2003/0123612 | A1 | * | 7/2003 | Pelc et al. ..................... 378/137 |
| 2004/0086081 | A1 | * | 5/2004 | Dahan et al. .................. 378/144 |
| 2004/0184579 | A1 | * | 9/2004 | Mihara et al. .................. 378/65 |
| 2005/0096532 | A1 | * | 5/2005 | Block et al. ................... 600/411 |
| 2005/0187459 | A1 | * | 8/2005 | Trequattrini et al. ......... 600/415 |
| 2005/0197564 | A1 | * | 9/2005 | Dempsey ...................... 600/411 |
| 2005/0267350 | A1 | * | 12/2005 | McKinnon .................... 600/407 |
| 2006/0184017 | A1 | * | 8/2006 | Kleen ........................... 600/434 |
| 2006/0273795 | A1 |   | 12/2006 | Rieke et al. |

FOREIGN PATENT DOCUMENTS

| GB | 2393373 A | 3/2004 |
| GB | 2427478 A | 12/2006 |
| GB | 2427479 A | 12/2006 |

(Continued)

*Primary Examiner* — Long V. Le
*Assistant Examiner* — Lawrence Laryea (57) ABSTRACT The invention relates to a combined radiation therapy and magnetic resonance unit. For this purpose, in accordance with the invention a combined radiation therapy and magnetic resonance unit is provided comprising a magnetic resonance diagnosis part with an interior, which is limited in radial direction by a main magnet, and a radiation therapy part for the irradiation of an irradiation area within the interior, wherein at least parts of the radiation therapy part, which comprise a beam deflection arrangement, are arranged within the interior.

19 Claims, 4 Drawing Sheets

(56) References Cited

FOREIGN PATENT DOCUMENTS

| JP | 63315072 A | 12/1988 |
| JP | 9502381 A | 3/1997 |
| JP | 10192268 A | 7/1998 |
| JP | 2001517132 A | 10/2001 |
| JP | 2004065808 A | 3/2004 |
| JP | 2005131408 A | 5/2005 |
| JP | 2006051064 A | 2/2006 |

* cited by examiner

COMBINED RADIATION THERAPY AND MAGNETIC RESONANCE UNIT

CROSS REFERENCE TO RELATED APPLICATIONS

This application claims priority of German application No. 10 2007 010 132.7 filed Feb. 28, 2007 and claims priority of German application No. 10 2008 007 245.1 filed Feb. 1, 2008, which are incorporated by reference herein in their entirety.

FIELD OF THE INVENTION

The invention relates to a combined radiation therapy and magnetic resonance unit.

BACKGROUND OF THE INVENTION

Generally in radiation therapy the aim is to irradiate a target within the human body in order to combat diseases, in particular cancer. For this purpose a high dose of radiation is specifically generated in an irradiation center (isocenter) of an irradiation apparatus. During irradiation the problem often arises that the irradiation target in the body can move. For instance, a tumor in the abdomen can move during breathing. On the other hand, in the period between radiation treatment planning and actual radiation treatment a tumor may have grown or have already shrunk. It was therefore proposed to check the position of the irradiation target in the body during radiation treatment by imaging, in order to control the beam or if necessary discontinue the irradiation, and thus increase the success of the therapy. This is in particular relevant for irradiation targets in the upper and lower abdomen as well as in the pelvic area, for example the prostate. To minimize the dose of radiation outside the target volume and thus protect healthy tissue, the entire radiation generation is moved around the patient. This concentrates the radiation dose in the beam in the area of the rotational axis.

Both X-ray and ultrasound systems were proposed as the imaging medium for monitoring the therapy. These, however, provide only a limited solution to the problem. In the case of ultrasound imaging the necessary penetration depth is lacking for many applications. In X-ray imaging the X-ray sensors can be disrupted or damaged by the gamma radiation of the accelerator. Furthermore, the quality of the tissue images is often unsatisfactory.

For this reason, at present mainly positioning aids and fixing devices or markings made on the skin of the patient are used to ensure that the patient is in the same position in the irradiation apparatus as decided in the radiation treatment planning and that the irradiation center of the irradiation apparatus is actually consistent with the irradiation target. These positioning aids and fixing devices are, however, expensive and in most cases they are also uncomfortable for the patient. In addition, they conceal the risk of irradiation errors because as a rule no further check of the actual position of the irradiation center is carried out during irradiation.

Magnetic resonance is a known technique which permits both particularly good soft-tissue imaging as well as spectroscopic analysis of the area being examined. As a result this technique is fundamentally suitable for monitoring radiation therapy.

In U.S. Pat. No. 6,366,798 a radiation therapy device is combined with various magnetic resonance imaging systems. In all the different versions mentioned here the magnet arrangement of the magnetic resonance imaging system is divided into two parts. In addition, in some versions key parts of the magnetic resonance imaging system rotate with the radiation source of the radiation therapy device. In each case the radiation source is outside the magnetic resonance imaging system and must be protected by means of shields from the stray field of the magnetic resonance imaging system. A division of the magnet, a rotatable magnet and shielding of the radiation source represent elaborate technical solutions and increase the cost.

In GB 2 427 479 A, U.S. Pat. No. 6,925,319 B2, GB 2 247 478 A, US 2005/0197564 A1 and US 2006/0273795 A1 further devices are described in which a radiation therapy device or an X-ray imaging system are combined with a magnetic resonance imaging system.

GB 2 393 373 A describes a linear accelerator with an integrated magnetic resonance imaging system. In one exemplary embodiment the magnetic resonance imaging system comprises means for compensation of a magnetic field in order to minimize the field strength of the magnetic field of the magnetic resonance imaging system at the location of the accelerator. In another exemplary embodiment a filter is used in order to compensate for possible heterogeneity caused in a therapy beam by the magnetic field of the magnetic resonance imaging system.

SUMMARY OF THE INVENTION

The object underlying the invention is therefore to provide a combined radiation therapy and magnetic resonance unit which with little constructional expense permits high-quality image monitoring by means of magnetic resonance during radiation therapy.

This object is achieved by the subject matter of the independent claim. Advantageous embodiments are described in the dependent claims.

In accordance with the invention a combined radiation therapy and magnetic resonance unit is provided comprising a magnetic resonance diagnosis part with an interior which is limited in radial direction by a main magnet, and a radiation therapy part for irradiation of an irradiation area within the interior, whereby at least parts of the radiation therapy part are located within the interior.

The magnetic diagnosis part permits a movement analysis of the irradiation target in real time and thus optimal monitoring and control of radiation therapy. The integration of the radiation therapy part in a magnetic resonance device and the resultant proximity of the radiation therapy part to the irradiation target permit a high radiation luminance as well as high accuracy in controlling the beam path. The use of a conventional main magnet is possible.

Advantageously, the radiation therapy part comprises an electron accelerator. Electrons are simple to generate and the accelerated electrons can easily generate a therapy beam.

In a particularly advantageous embodiment an electron beam direction runs essentially parallel to the axis of the main magnetic field in the electron accelerator. Electrons which move parallel to a magnetic field are not influenced by it in their flight path. It is therefore easier to determine their flight direction and speed compared with electrons influenced or accelerated by magnetic fields.

Advantageously, the radiation therapy part comprises a beam deflection arrangement which in particular comprises an electromagnet which deflects the electron beam inward into the interior. In this way the accelerated electrons are directed into the desired therapy beam direction.

In a particularly advantageous embodiment the beam deflection arrangement comprises a pulsed magnet. This can (briefly) generate a magnetic field as big as the main magnetic field or bigger without any particular expense. Moreover, by using particularly short pulses, disruption of the magnetic resonance device is minimized.

Expediently, the radiation therapy part comprises a target anode to produce an X-ray beam along an X-ray beam path. X-ray radiation, in particular high-energy X-ray radiation, is particularly suitable for radiation therapy and is not influenced by the electromagnetic fields prevailing in a magnetic resonance device.

In a particularly advantageous embodiment the target anode is a transmission anode. A transmission anode is particularly suitable for generating high-energy X-ray radiation.

In a further embodiment a homogenizing body is arranged in the X-ray beam path after the target anode. The homogenizing body for example weakens the beam core and homogenizes the X-ray beam distribution in the beam cross-section.

Advantageously, a collimator is arranged in the X-ray beam path after the target anode. The collimator enables the direction of the X-ray beam and the cross-section of the X-ray beam to be regulated.

In a particularly advantageous embodiment the collimator is arranged at least partially between two axially distanced partial gradient coils of the magnetic resonance device. This represents a particularly space-saving arrangement and at the same time provides for advantageous proximity to the irradiation target.

In a further advantageous embodiment the collimator comprises adjusters for changing the cross-section of the X-ray beam. As a result, the cross-section of the X-ray beam can be ideally adapted to the shape of the irradiation target.

At least partial gradient coils of the gradient coil system are advantageously shielded against the radiation therapy part. This permits independent, in particular also simultaneous, operation of the radiation therapy part, which rotates in operation, and of the magnetic resonance diagnosis part as the changing gradient fields of the gradient coils in this way do not influence the rotating radiation therapy part.

If the radiation therapy part is rotatable around the axis of the main magnetic field the further advantage results that the applied dose of radiation outside the target volume, i.e. outside the irradiation center, can be minimized. This means that adverse effects on healthy tissue during radiation therapy are reduced.

BRIEF DESCRIPTION OF THE DRAWINGS

Further advantages and details of the invention will emerge from the exemplary embodiment described below and with reference to the drawing. The examples listed do not represent a restriction of the invention. The figures show.

DETAILED DESCRIPTION OF THE INVENTION

Figure 1:
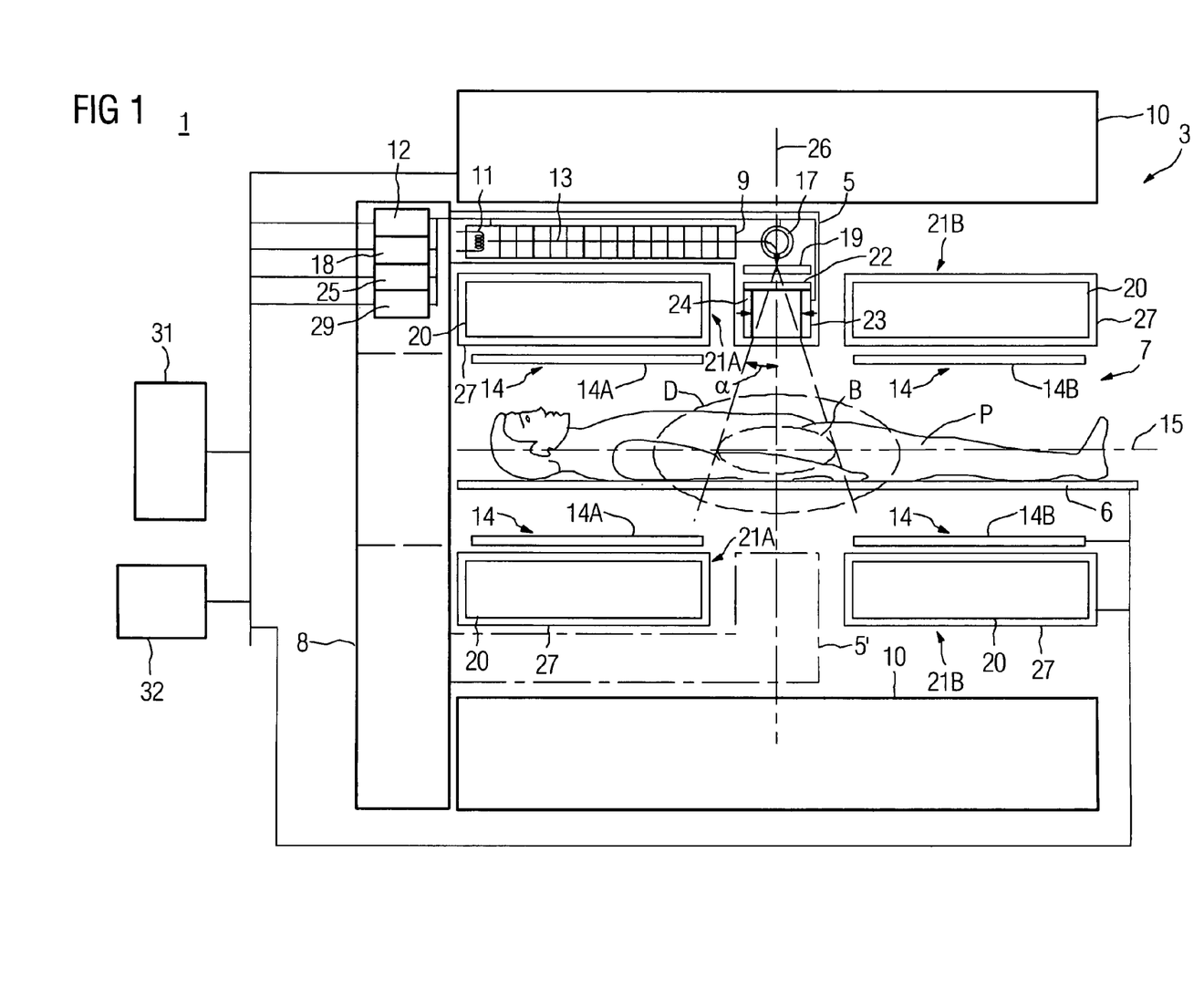
FIG. 1 a schematic representation of a combined radiation therapy and magnetic resonance unit in accordance with the invention, FIGS. 2-4 schematic representations of segments of further configurations of a combined radiation therapy and magnetic resonance unit in accordance with the invention, and FIGS. 5-8 exemplary configurations of beam deflection arrangements which can be used in a combined radiation therapy and magnetic resonance unit in accordance with the invention.

FIG. 1 shows a schematic representation (not to scale) of a combined radiation therapy and magnetic resonance unit 1 with a magnetic resonance diagnosis part 3 and a radiation therapy part 5. The magnetic resonance diagnosis part 3 comprises a main magnet 10, a gradient coil system comprising two in this case symmetrical partial gradient coils 21A,21B, high-frequency coils 14, for example two parts of a body coil 14A,14B, and a patient bed 6 for a patient (P). All these components of the magnetic resonance part are connected to a control unit 31 and an operating and display console 32.

In the example presented, both the main magnet 10 and the partial gradient coils 21A,21B are essentially shaped like a hollow cylinder and arranged coaxially around the horizontal axis 15. The inner shell of the main magnet 10 limits in radial direction (facing away vertically from the axis 15) a cylinder-shaped interior 7, in which the radiation therapy part 5, the gradient system, high-frequency coils 14 and the patient bed 6 are arranged. More precisely the radiation therapy part 5 is located in the interior 7 between the outer side of the gradient coil system 21A and 21B and the inwardly facing shell surface of the main magnet 10.

In addition to the magnet coils the main magnet 10 comprises further structural elements, such as supports, housing etc., and generates the homogenous main magnetic field necessary for the magnetic resonance examination. In the example shown the direction of the main magnetic field is parallel to the horizontal axis 15. High-frequency excitation pulses which are irradiated by means of high-frequency coils 14 are used to excite the nuclear spins of the patient. The signals emitted by the excited nuclear spins are also received by high-frequency coils 14.

The axially distanced partial gradient coils 21A,21B in each case comprise gradient coils 20, which are in each case completely enclosed by a shield 27. The gradient coil 20 comprises supports and individual gradient coils which irradiate magnetic gradient fields for selective layer excitation and for location-coding of the magnetic resonance signals in three spatial directions.

The radiation therapy part 5 is arranged on a gantry 8 and comprises an electron accelerator 9, which here is configured as a linear accelerator, a beam deflection arrangement 17, a target anode 19, a homogenizing body 22 and a collimator 23. The gantry 8 can feature a recess (broken lines), by which access to the magnetic resonance diagnosis part remains possible also from this side.

The electron accelerator 9 of the radiation therapy part 5 comprises an electron source 11, for example a tungsten cathode, which generates an electron beam 13, which is accelerated by the electron accelerator 9 preferably pulsed parallel to the main magnetic field of the main magnet 10. The electron accelerator 9 for example generates electron beam pulses with a length of 5 μs every 5 ms. If the electron accelerator 9 generates pulsed electron beams 13, it can be built more compactly, e.g. with a length of about half a meter, and still withstand the impact of the high-energy electron beams 13.

The electrons of the electron beam 13 are accelerated by electric alternating fields in cylinder-shaped hollow conductors of the electron accelerator 9. The electrons of the electron beam 13 are accelerated to energies up to a magnitude of several MeV. The electron accelerator 9 is connected to an accelerator control unit 12 to control the alternating fields and the electron source 11.

The electron beam 13 leaves the electron accelerator 9 at the end opposite the electron source and is deflected by the beam deflection arrangement 17 through 90° radially inward in the direction of axis 15. For this purpose the beam deflection arrangement 17 comprises a magnet which generates a suitable magnetic field. The magnet is configured as an electromagnet made of non-ferromagnetic materials to prevent undesired interaction with the surrounding magnetic fields.

As the beam deflection arrangement 17 has to work in a strong, outer magnetic field, it has been modified compared with conventional beam deflection arrangements.

To be able to deflect the pulsed electron beam 13 in a small space, the beam deflection arrangement 17 must generate strong magnetic fields. To reduce the power loss, the magnetic field of the beam deflection arrangement 17 is a pulsed magnetic field which is synchronized with the pulsed electron beam 13. For this purpose the beam deflection arrangement 17 is connected to a beam deflection control unit 18 which is also connected to the accelerator control unit 12.

The deflected electron beam 13 hits the target anode 19 and generates an X-ray beam that emerges from the target anode in the beam elongation along an X-ray beam path. The X-ray beam is homogenized by the homogenizing body 22.

The collimator 23 is arranged in an annular slot between the distanced partial gradient coils 21A, 21B in the X-ray beam after the target anode 19. The proximity to the irradiation target thus achieved improves the radiation luminance and also the effectiveness of the collimator 23.

The collimator 23 enables the direction of the X-ray beam and the cross-section of the X-ray beam to be influenced. For this purpose the collimator 23 incorporates moveable adjusters 24, which permit the X-ray beam to pass only in a certain direction, e.g. only parallel to the radial axis 26 or up to at most in one direction through an angle $\alpha$ away from the axis 26, and only with a certain cross-section. It is also possible to set the adjusters 24 of the collimator 23 in such a way that no X-ray beams can pass parallel to the axis 26 and only angled X-ray beams in one direction through certain angles away from the axis 26 can pass through. To control the adjusters 24 the collimator 23 is connected to a collimator control unit 25. Such collimators are adequately known. By way of example reference can be made to multi-leaf collimators. They make it possible to perform intensity modulated radiation therapy (IMRT), in which the size, shape and intensity of the X-ray beam can be optimally adapted to the irradiation target. In particular IMRT also enables the irradiation center to be positioned outside the rotational axis of the radiation therapy device.

The X-ray beam penetrates the examination subject, in this case the patient P, and the X-ray beam path runs through a diagnosis volume D of the magnetic resonance diagnosis part 3. To minimize the local dose of radiation outside the irradiation target volume, the radiation therapy part rotates around the axis of the main magnetic field. As a result, the full dose is applied only in the irradiation center B. The collimator 23 constantly adapts the cross-section of the X-ray beam to the actual outline of the irradiation target even during rotation. The gantry 8 is configured for rotation of the radiation therapy part. A gantry control unit 29 controls the movement of the radiation therapy part 5. As an example the radiation therapy part 5 is shown as radiation therapy part 5' after rotation through 180°.

The gantry control unit 29, the collimator control unit 25, the beam deflection control unit 18, the accelerator control unit 12 and the control unit 31 are connected to each other so that the diagnosis data collected by the magnetic resonance diagnosis part, for example the three-dimensional shape of the irradiation target, the rotational position of the radiation therapy part, as well as the collimator settings with regard to cross-section and direction of the X-ray beam and the generation of pulsed beams described above can be coordinated with each other.

The patient bed 6 is preferably moveable in three spatial directions so that the target area of the irradiation can be positioned precisely in the irradiation center B. For this purpose the control unit 31 is expediently configured for controlling a movement of the patient bed.

Figure 2:
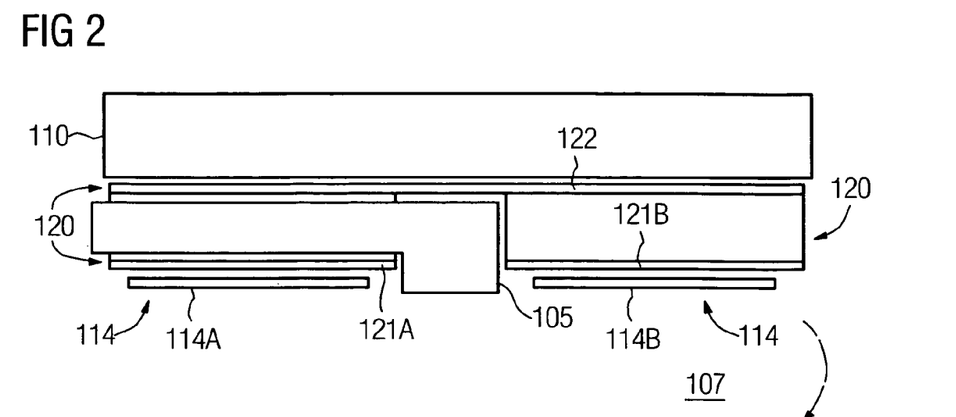
Figure 3:
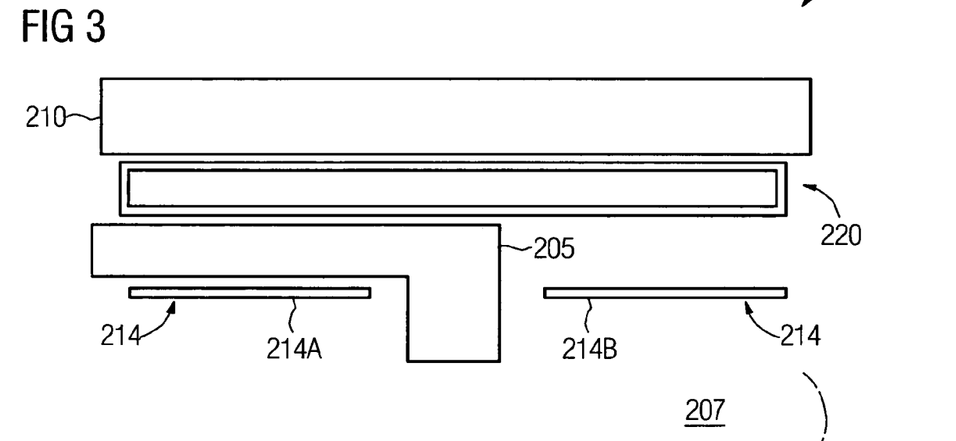
Figure 4:
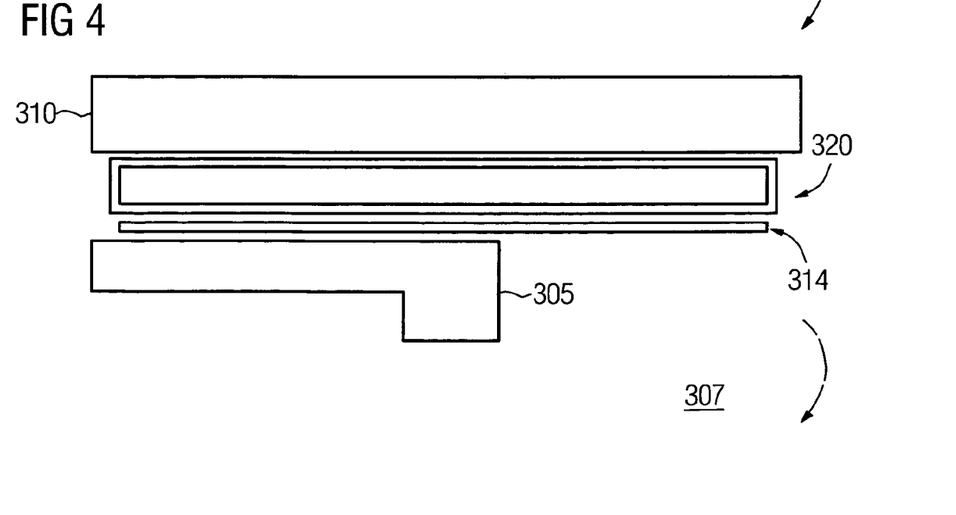

FIGS. 2 to 4 show segments of further exemplary configurations of a combined radiation therapy and magnetic resonance unit in accordance with the invention. In the exemplary configurations shown in particular the arrangement of a respective radiation therapy part 5, 105, 205, 305 varies from the exemplary embodiment in FIG. 1. For the sake of clarity, therefore, only the upper section of a main magnet 110, 210, 310 of the combined radiation therapy and magnetic resonance unit up to about one high-frequency coil 114, 214, 314 of the combined radiation therapy and magnetic resonance unit is shown. The rest of the configuration and its mode of operation are, unless otherwise described, essentially the same as in the example shown in FIG. 1, to which reference is hereby made.

FIG. 2 shows a main magnet 110 of the combined radiation therapy and magnetic resonance unit on whose side facing an interior 107 of the combined radiation therapy and magnetic resonance unit a gradient coil system 120 is arranged. The gradient coil system 120 comprises in particular primary coils 121 and secondary coils 122. Between primary coils 121 and secondary coils 122 a free space is located in which the radiation therapy part 105 of the combined radiation therapy and magnetic resonance unit is arranged. Such a distanced arrangement of the primary and secondary coils 121 and 122 increases the efficiency of the gradient coil system 120. In addition, high-frequency coils 114 are arranged on the side of the gradient coil system facing the interior 107.

The gradient coil system 120 or at least the primary coils 121 as shown in the example in FIG. 1 can be divided into two partial gradient coils 121A, 121B and arranged in such a way that at least parts of the radiation therapy part 105 can move in an annular space between the parts in a rotation of the radiation therapy part 105 around the axis of the main magnetic field. In this case the high-frequency coils 114 are also advantageously divided correspondingly into two partial high-frequency coils 114A and 114B.

Alternatively it is conceivable for the gradient coil system 120 to be configured in such a way that together with the radiation therapy part 105 it can rotate around the axis of the main magnetic field. In this case a division of the gradient coil system 120 or of the primary coils is not absolutely appropriate. It suffices to configure the primary coil 121 in such a way that it can let the radiation therapy part 105 penetrate into the interior 107 at one point in order to emit the therapy beams onto an irradiation center B. The same applies to the high-frequency coils 114. It may be necessary here to compensate for the mechanical turning of the gradient coil system 120 by suitable activation of the gradient currents. Such an electric rotation of gradient fields is, however, a usual capability of standard magnetic resonance systems. Nevertheless, high requirements should be imposed on the accuracy and reproducibility of the rotation.

Thanks to its particularly compact design this exemplary embodiment gives the patient an exceptional amount of room in the interior 107. Advantageously, a collimator of the radiation therapy part 105 is incorporated in a particularly flat configuration in the exemplary embodiment shown in FIG. 2 in order to give the patient even more room in the interior 107 of the combined radiation therapy and magnetic resonance unit.

FIG. 3 presents a segment of a further exemplary embodiment of a combined radiation therapy and magnetic resonance unit. In this exemplary embodiment a gradient coil system 220 as in a standard magnetic resonance device is arranged on the side of a main magnet 210 facing an interior 207 of the combined radiation therapy and magnetic resonance unit. Standard components can be used for the main magnet 210 and the gradient system 220, which among other things reduces cost.

Again on the side of the gradient system 220 facing the interior 207 high-frequency coils 214 are arranged. Between the gradient system 220 and the high-frequency coils 214, however, adequate space is left in order to arrange a radiation therapy part 205 of the combined radiation therapy and magnetic resonance unit between the gradient system 220 and the high-frequency coils 214.

During irradiation of an irradiation center B the radiation therapy part 205 rotates around the main magnetic field axis of the combined radiation therapy and magnetic resonance unit. In a similar way as in the exemplary embodiment of FIG. 2 the high-frequency coils 214 can here too either be divided into two partial high-frequency coils 214A and 214B in such a way that at least parts of the radiation therapy part 205 can move in an annular gap between the partial high-frequency coils 214A and 214B. Or the high-frequency coils 214 can be rotated with the radiation therapy part 205.

FIG. 4 shows schematically a segment of a further exemplary embodiment of a combined radiation therapy and magnetic resonance unit. In this case, as in a conventional design of a magnetic resonance unit, high-frequency coils 314 are arranged within a gradient system 320 which itself is arranged within a main magnet 310. A radiation therapy part 305 is arranged on the side facing an interior 307 of the combined radiation therapy and magnetic resonance unit. As in the exemplary embodiments presented above the radiation therapy part 305 rotates during irradiation around the main magnetic field axis of the combined radiation therapy and magnetic resonance unit. In this exemplary embodiment no particular structural measures are necessary with regard to the gradient system 320 and the high-frequency coils 314 to make this rotational movement of the radiation therapy part possible.

Advantageously the inner radius of the high-frequency coils 314 is as big as possible and the radiation therapy part is as flat as possible so that the patient is not cramped in the interior 307.

The radiation therapy part 105,205,305 of the exemplary embodiments in FIGS. 2 to 4 in each case incorporates essentially the same construction as the radiotherapy part 5 from the exemplary embodiment in FIG. 1. For the sake of clarity the individual components are not shown again. The rotational movement of the radiation therapy parts 105,205,305 and/or the gradient coil system 120,220,320 and/or the high-frequency coils 114,214 is indicated in each case by a broken-line arrow.

If necessary, in the exemplary embodiments of FIGS. 2, 3 and 4 the radiation therapy part 105,205,305 and the magnetic resonance part, in particular the gradient system 120,220,320 and/or the high-frequency coils 114,214,314, are not operated at the same time but are alternated in order to exclude possible disruptive interaction, in particular between moving parts of the radiation therapy part 105,205,305 and electromagnetic alternating fields of the magnetic resonance part.

FIGS. 5 to 8 show three examples of possible configurations of beam deflection arrangements 17 which can be used in a radiation therapy part 5,105,205,305.

Figure 5:
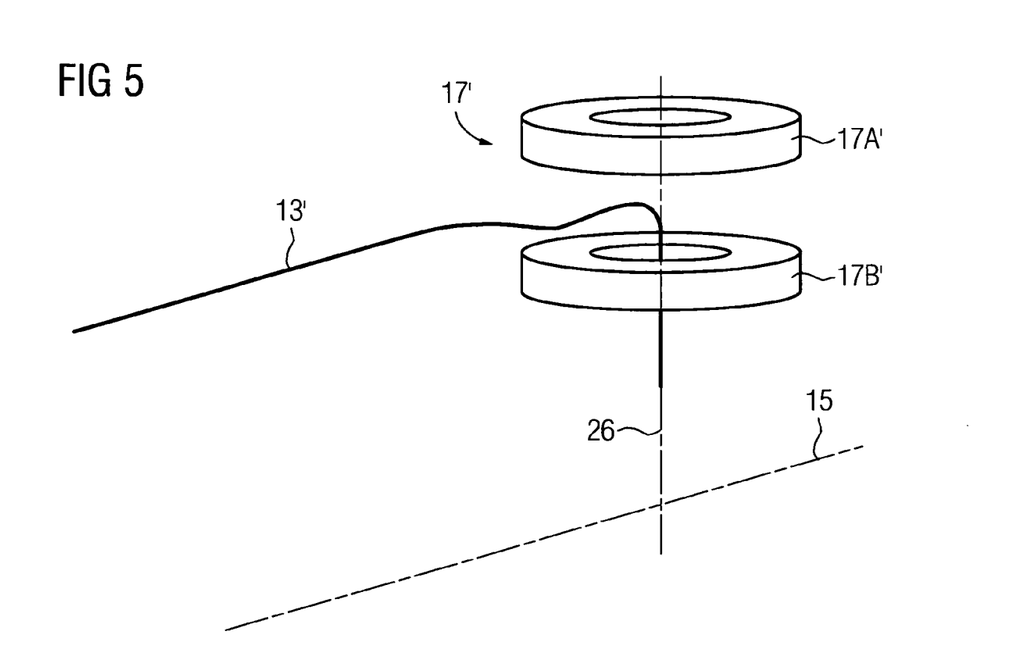

FIG. 5 shows a beam deflection arrangement 17' which consists of two annular deflection coils 17A' and 17B'. The deflection coils 17A',17B' are arranged in a combined radiation therapy and magnetic resonance unit essentially vertically to the main magnetic field of the main magnet of the combined radiation therapy and magnetic resonance unit. The field direction of the deflection coils 17A',17B' runs essentially parallel to a radial axis 26 of the combined radiation therapy and magnetic resonance unit, i.e. in the direction of exit desired for a therapy beam. Through the combination of the main magnetic field and the magnetic field of the deflection coils 17A',17B' an electron beam 13' is deflected in the desired direction.

The current density in the deflection coils 17A',17B' must be determined among other things according to the main magnetic field strength of the combined radiation therapy and magnetic resonance unit and energy of the electron beam. For example, with an electron beam of 6 MeV and a main magnetic field of 1,5T the deflection coils 17A',17B' can deflect the beam in the desired direction if the current density in the deflection coils 17A',17B' amounts to approx. 500 MA/m$^2$.

Figure 6:
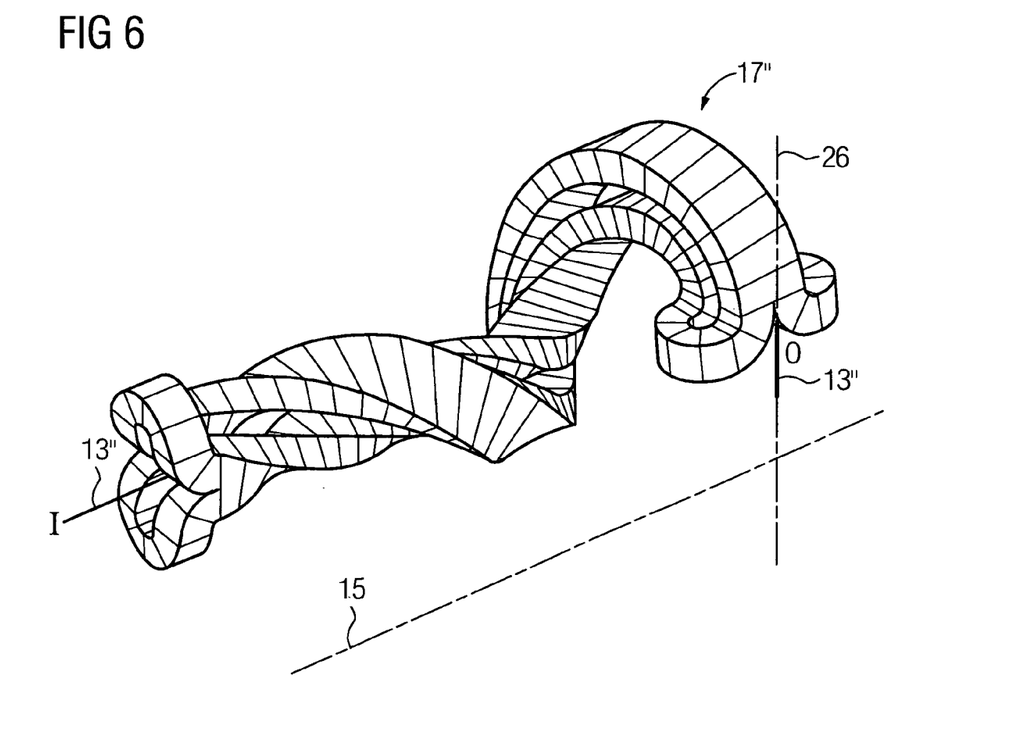
Figure 7:
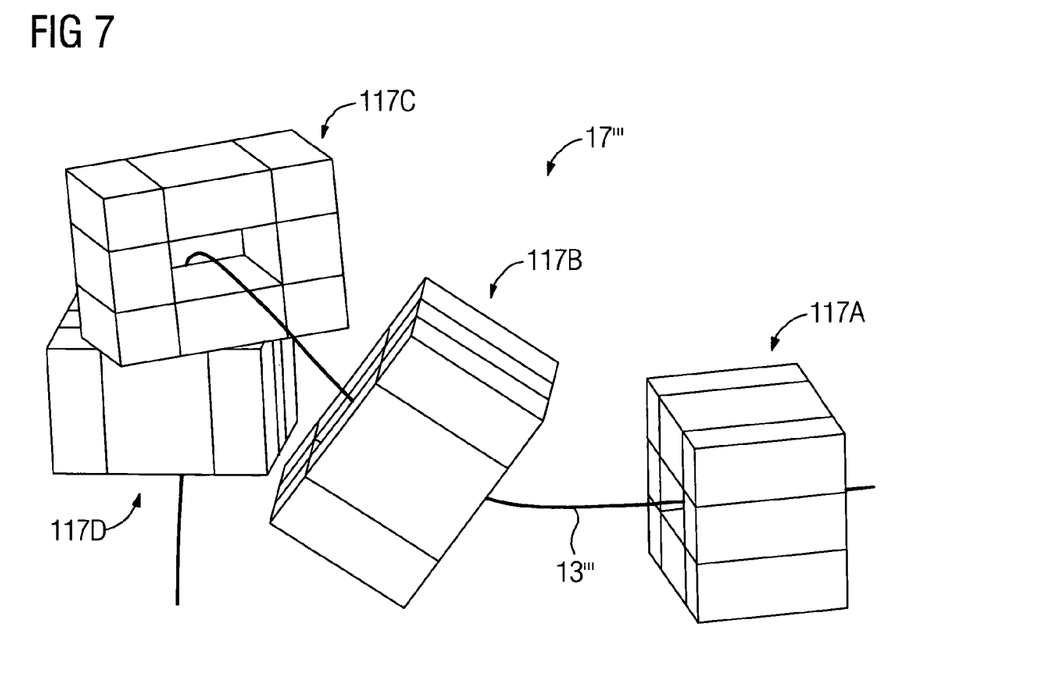
Figure 8:
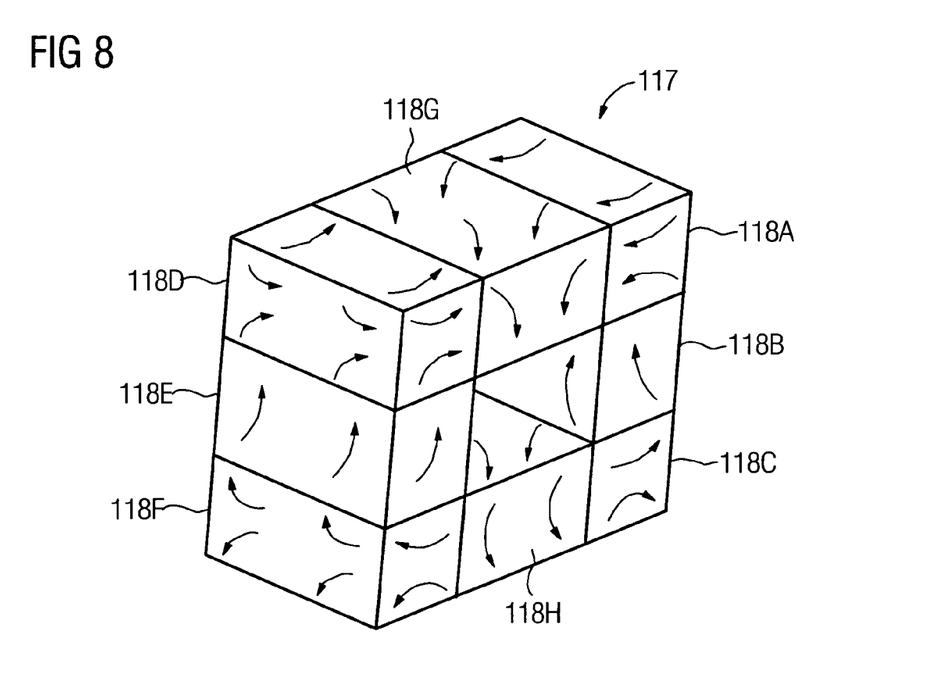

FIGS. 6 to 8 show beam deflection arrangements 17" and 17''', whose configurations were calculated by means of computer simulation programs, for example based on a finite elements method or a finite differences method. In each case the underlying problem was the question as to how an electron beam which enters a main magnetic field in a parallel direction can be deflected in a direction which is vertical to the main magnetic field in order to hit a target. For this purpose, the field necessary for such deflection and how it can be produced were calculated.

FIG. 6 shows an active coil pair 17" as the beam deflection arrangement which is shaped in such a way that it solves the problem posed. An electron beam 13" arriving parallel to a horizontal axis 15, and therefore in the direction of a main magnetic field of a combined radiation therapy and magnetic resonance system, enters between the coil pair 17" at the position "I" and is guided in such a way that it leaves the coil pair 17" parallel to a radial axis 26 of the combined radiation therapy and magnetic resonance unit at the position "O". The strength of the field strength of the coil pair 17" can be varied according to the energy of the electron beam.

An exemplary coil pair 17" generates a quadrature-axis field of approx. 0.3T. As a result, e.g. an electron beam of 6 MeV can be deflected in a combined radiation therapy and magnetic resonance unit of 1.5 T field strength in the desired way.

FIGS. 7 and 8 present a further possible solution of the above-mentioned problem, this time using a passive beam deflection arrangement.

As shown in FIG. 7, the beam deflection arrangement 17''', which generates the quadrature-axis field necessary for solving the problem, comprises four deflection units 117A,B,C, D. The arrangement of the deflection units 117A,B,C,D was determined by iteration in such a way that an electron beam 13''' entering parallel to a main magnetic field as shown in FIG. 7 from the right into the deflection unit 117A is deflected in such a way by deflection unit 117A to deflection unit 117B that the electron beam 13''' is deflected upward through deflection unit 117B. From deflection unit 117B the electron beam 13''' is deflected by deflection unit 117C, whereby the electron beam 13" leaves the deflection unit 117C in such a way that it is deflected downward to deflection unit 117D, so that it leaves deflection unit 117D vertically to the main magnetic field. References such as "upward", "downward", "right" and "left" relate in each case to the example shown in FIG. 7.

FIG. 8 shows more precisely a deflection unit 117. The deflection unit 117 comprises several permanent magnets 118A,B,C,D,E,F,G,H, which are preferably made of rare earths, e.g. NdFeB or SmCo.

For example, to deflect a 6 MeV electron beam in a main magnetic field of 1.4 T in the desired way, six permanent magnets 118A,B,C,D,E,F with dimensions of approx. 10×4×4 mm and two permanent magnets 118G,H with dimensions of 10×8×4 mm are arranged as shown. In each case three of the permanent magnets of the smaller size 118A, B,C,D,E,F are stacked on top of each other with alternating direction of the respective magnetic fields of the permanent magnets 118A,B,C,D,E,F. The two larger permanent magnets 118G,H are arranged between this stack. The arrows indicate the respective magnetic field directions in the permanent magnets 118A,B,C,D,E,F,G,H.

This configuration is particularly easy to produce and, furthermore, forms a particularly compact solution. In addition, only low static forces are exerted here, so that no particular fastening measures are needed. Furthermore, initial results show that the beam deflection arrangement 17''' produces only a very small stray field. However, permanent magnets are sensitive to changes in the ambient temperature or the surrounding main magnetic field.

The invention claimed is:

1. A combined radiation therapy and magnetic resonance unit, comprising:
    a magnetic resonance device with an annular interior space arranged to longitudinally extend along an axial direction to receive the body of a patient, wherein the annular interior space is circumferentially limited in a radial direction perpendicular to the axial direction by a main magnet comprising magnetic coils, wherein the main magnet is disposed at a first radial distance along the radial direction to longitudinally continually enclose the annular interior space which receives the body of the patient; and
    a radiation therapy device that irradiates an area of the body of the patient within the annular interior space,
    wherein a portion of the radiation therapy device is disposed at a second radial distance along the radial direction, the second radial distance being shorter than the first radial distance so that the portion of the radiation therapy device is within the annular interior space that is circumferentially limited in the radial direction by the main magnet.

2. The combined radiation therapy and magnetic resonance unit as claimed in claim 1, wherein the radiation therapy device is arranged in a space selected from the group consisting of: between a shell surface of the main magnet limiting the annular interior space and an outer side of a gradient coil system coaxial to the main magnet, between a primary coil and a secondary coil of a gradient coil system, between a gradient coil system and a high-frequency coil, and on a side of a high-frequency coil facing the annular interior space.

3. The combined radiation therapy and magnetic resonance unit as claimed in claim 1, wherein the radiation therapy device comprises an electron accelerator that runs parallel to an axis of a main magnetic field generated by the main magnet.

4. The combined radiation therapy and magnetic resonance unit as claimed in claim 3, wherein the electron accelerator is connected to an accelerator control unit.

5. The combined radiation therapy and magnetic resonance unit as claimed in claim 1, wherein the radiation therapy device comprises a beam deflection arrangement.

6. The combined radiation therapy and magnetic resonance unit as claimed in claim 5, wherein the beam deflection arrangement deflects an electron beam inward into the interior.

7. The combined radiation therapy and magnetic resonance unit as claimed in claim 6, wherein the beam deflection arrangement deflects the electron beam through 90° radially inward into the annular interior space.

8. The combined radiation therapy and magnetic resonance unit as claimed in claim 5, wherein the beam deflection arrangement comprises a magnet selected from the group consisting of: an electromagnet, a permanent magnet, and a pulsed magnet.

9. The combined radiation therapy and magnetic resonance unit as claimed in claim 5, wherein the beam deflection arrangement is connected to a beam deflection control unit.

10. The combined radiation therapy and magnetic resonance unit as claimed in claim 1, wherein the radiation therapy device comprises a target anode to generate an X-ray beam along an X-ray beam path.

11. The combined radiation therapy and magnetic resonance unit as claimed in claim 10, wherein the target anode is a transmission anode.

12. The combined radiation therapy and magnetic resonance unit as claimed in claim 10, wherein a homogenizing body is arranged in the X-ray beam path after the target anode.

13. The combined radiation therapy and magnetic resonance unit as claimed in claim 10, wherein a collimator is arranged in the X-ray beam path after the target anode.

14. The combined radiation therapy and magnetic resonance unit as claimed in claim 13, wherein the collimator is arranged between two axially distanced partial gradient coils of the magnetic resonance device.

15. The combined radiation therapy and magnetic resonance unit as claimed in claim 13, wherein the collimator comprises an adjuster to change a cross-section of the X-ray beam.

16. The combined radiation therapy and magnetic resonance unit as claimed in claim 13, wherein the collimator is connected to a collimator control unit.

17. The combined radiation therapy and magnetic resonance unit as claimed in claim 1, wherein a partial of a gradient coil system of the magnetic resonance device is shielded from the radiation therapy device.

18. The combined radiation therapy and magnetic resonance unit as claimed in claim 1, wherein the radiation therapy device is rotatable around an axis of a main magnetic field generated by the main magnet.

19. A combined radiation therapy and magnetic resonance unit, comprising:
    a magnetic resonance device defining an annular space along a longitudinal axis, the magnetic resonance device having a radial axis perpendicular to the longitudinal axis;
    a main magnet of the magnetic resonance device disposed at a first radial distance along the radial axis to surround the annular space; and
    a radiation therapy device to irradiate a volume in the annular space,
    wherein a portion of the radiation therapy device is disposed at a second radial distance along the radial axis, the second radial distance being shorter relative to the first radial distance so that the portion of the radiation therapy device is radially surrounded by the main magnet.

* * * * *